United States Patent [19]

Raines

[11] Patent Number: 4,687,473
[45] Date of Patent: Aug. 18, 1987

[54] SELF-CONTAINED SECONDARY SOLUTION SET

[75] Inventor: Kenneth Raines, Bethlehem, Pa.

[73] Assignee: Burron Medical Inc., Bethlehem, Pa.

[21] Appl. No.: 826,096

[22] Filed: Feb. 6, 1986

[51] Int. Cl.$^4$ ............................................... A61M 5/14
[52] U.S. Cl. ................................... 604/251; 604/246; 604/409
[58] Field of Search ........................ 604/251, 246, 409

[56] References Cited

U.S. PATENT DOCUMENTS

| | | | |
|---|---|---|---|
| 2,129,983 | 9/1938 | Bacon | 604/251 |
| 2,210,098 | 8/1940 | Ravenscroft | 604/251 |
| 2,352,349 | 6/1944 | Shaw | 604/251 |
| 2,770,234 | 11/1956 | Nesset et al. | 604/246 |
| 3,625,211 | 12/1971 | Butler | 604/246 |
| 3,774,603 | 11/1973 | McPhee | 604/246 |
| 3,881,640 | 5/1975 | Noble | 604/246 |
| 3,939,832 | 2/1976 | Miller | 604/251 |
| 3,951,145 | 4/1976 | Smith | 604/246 |
| 4,078,563 | 3/1978 | Tuseth | 604/246 |
| 4,175,558 | 11/1979 | Hess, III et al. | 604/246 |
| 4,332,247 | 6/1982 | Mittleman | 604/251 |
| 4,387,734 | 6/1983 | Borsanyi | 604/251 |
| 4,553,964 | 11/1985 | Sasaki | 604/251 |

FOREIGN PATENT DOCUMENTS 1182016 2/1970 United Kingdom ............... 604/251

Primary Examiner—C. Fred Rosenbaum
Assistant Examiner—John D. Ferros
Attorney, Agent, or Firm—Shoemaker and Mattare, Ltd.

[57] ABSTRACT

A self-contained I.V. set for infusing drugs and secondary medications is disclosed. A mini-I.V. container having a filtered air vent and a valved filling port is filled by a disposable syringe. A drip chamber below the mini-I.V. container receives medication through a drip device at the bottom of the container. From the drip chamber, the medication enters a small bore tube equipped with a roller clamp and an infusion needle fitting. A convenient hanger for the device is provided.

11 Claims, 10 Drawing Figures

4,687,473

SELF-CONTAINED SECONDARY SOLUTION SET

BACKGROUND OF THE INVENTION

The present invention relates to a self-contained solution set particularly for administering secondary medications but also useful for the infusion of small amounts of any medication, such as in the range of 10-50 ml. of medication.

An object of the invention is to provide a secondary solution set which is more convenient to use, more reliable in its operation, and safer than known prior art devices.

A further object of the invention is to provide a device of the mentioned character which includes a molded mini-I.V. container having a valved filling port and a filtered air inlet, whereby the container can be filled by means of a disposable syringe, without needle, through the filling port of the container without providing a vent for the barrel of the syringe.

Other objects of the invention are to provide a secondary solution set having a lower profile without the filling syringe, a more convenient hanging means for the device, and the avoidance of an exposed syringe plunger in the device itself.

Still another object is to provide a self-contained solution set of the character mentioned which may, if desired, by filled at the pharmacy and which may be used to infuse multiple drugs from the same set, the device performing like a small I.V. bag.

Other features and advantages of the invention will become apparent to those skilled in the art during the course of the following detailed description.

DETAILED DESCRIPTION

Figure 1:
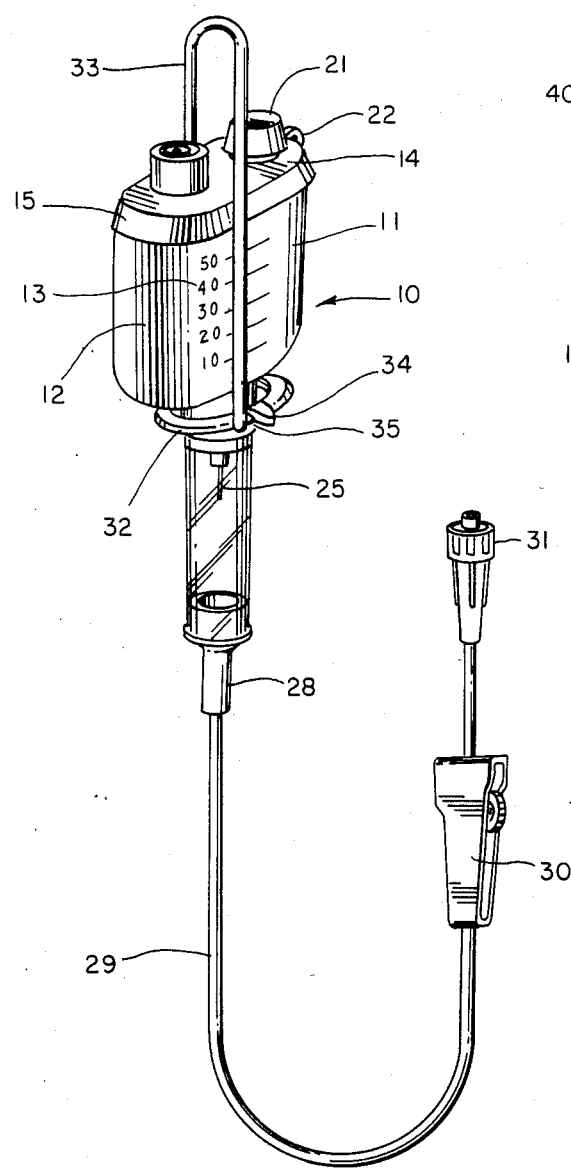
FIG. 1 is a perspective view of a self-contained secondary solution set according to the present invention.

Referring to the drawings in detail wherein like numerals designate like parts, a self-contained solution set 10, FIG. 1, comprises a molded mini-container 11 including a body portion 12 adapted to hold a relatively small amount of solution in the range of 10-50 ml., for example. Preferably the side wall of the small container 11 is graduated in mls. over this range, as shown at 13 in FIG. 1.

The container 11 includes a top 14 having a marginal skirt 15 which is permanently attached to a mating tapered flange 16 of the container body portion 12 by a solvent or by known sonic means. In any case, an airtight seal is formed between the open top container body portion 12 and the container top or cover 14.

The molded container is equipped on its top 14 with a small air vent 17 covered by a shrouded air filter 18 to prevent the creation of an air lock in the container 11. A filling port 19 is also provided on the container top 14, having a suitable valve 20. The nature of this valve can vary depending on circumstances. It can be a rubber stopple or membrane, or other rubber injection site, a duckbill valve or other known valve means. The arrangement allows the container 11 to be filled by a disposable syringe, with the syringe separated from the solution set after filling to provide a low profile for the device. In some cases, the syringe, not shown, could remain attached to the container 11. The arrangement allows the container 11 to be filled at the pharmacy or at the location of use.

Various single or multiple medications can be infused by the mini-I.V. set which operates like an ordinary I.V. bag by gravity flow. In some cases, a powdered drug or medication can be installed in the container 11 and a reconstituting liquid is then injected from a disposable syringe through the filling port 19. The solution set itself, according to the invention, avoids the use of any exposed syringe plunger.

A protective closure cap 21 for the filling port 19 is provided, and is attached to the container top 14 by an integral flexible tether 2.

At its bottom, the container body portion 12 is equipped with a tapered nipple 23 receiving an adapter 24 of a drip device 25. A short sleeve 26 surrounds the drip device and is formed integrally with the bottom wall of container body portion 12. A tubular drip chamber 27 has its top end telescoped over the sleeve 26 and secured thereto by gluing.

A tubing adapter 28 is secured by gluing in the bottom end portion of the drip chamber 27 and a length of small bore PVC tubing 29 extends from the adapter 28 and is equipped with a conventional roller clamp 30. At its remote end, the tube section 29 carries a male LUER-LOCK fitting 31 enabling attachment of a suitable infusion needle, not shown, to the unit.

Figure 7:
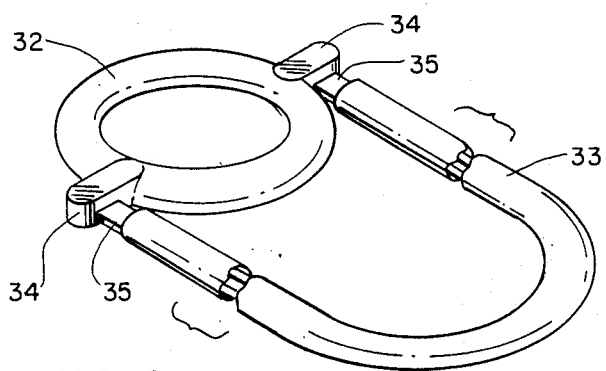
FIG. 7 is a perspective view of a hanger for the device.

A hanger for the solution set 10 comprises a ring 32, FIG. 7, which engages beneath the bottom wall of the container body portion 12 and surrounds the drip chamber 27. An elongated hanger loop 33 has its opposite ends attached to side ears 34 of the ring 32 by integral flexible hinges 35. The hanger loop 33 has its two arms or sides spaced apart sufficiently to straddle the mini-container 11 when the unit is in use and hanging from a support element, not shown.

Figure 4:
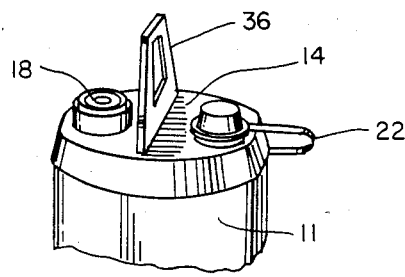
FIG. 4 is a fragmentary perspective view showing a modification of the hanging means for the device.

FIG. 4 of the drawings shows a variant of the hanger means in which a short apertured hanger element 36 is formed integrally with the molded top 14 of the container 11. In all other respects, the device is identical to the structure described previously relative to FIGS. 1, 2, 3, and 7.

Figure 5:
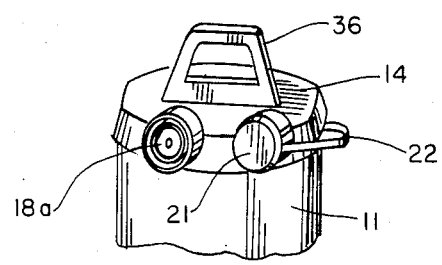
FIG. 5 is a similar view showing a modification of the filtered air vent and filling port.
Figure 6:
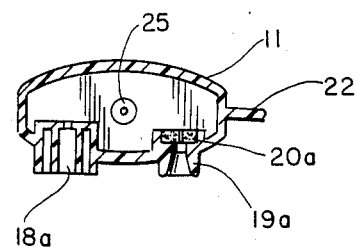
FIG. 6 is a horizontal cross section taken through the filtered air vent and valved filling port.

FIGS. 5 and 6 show another variant of the invention in which the filtered air vent 18a and filling port 19a with valve 20a are formed on the side of the container 11 instead of on its top. Otherwise, the device is identical in its construction and operation to the previously-described embodiments.

Figure 2A:
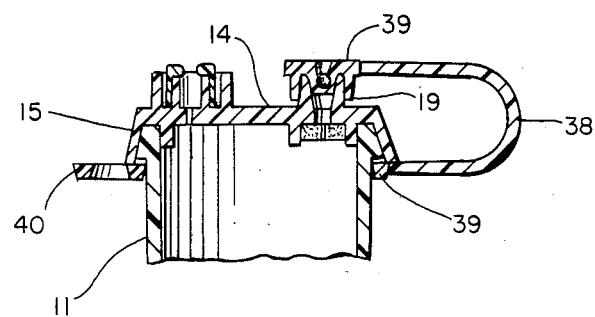
FIG. 2A is a view similar to FIG. 2 showing a modification of the invention.
Figure 2:
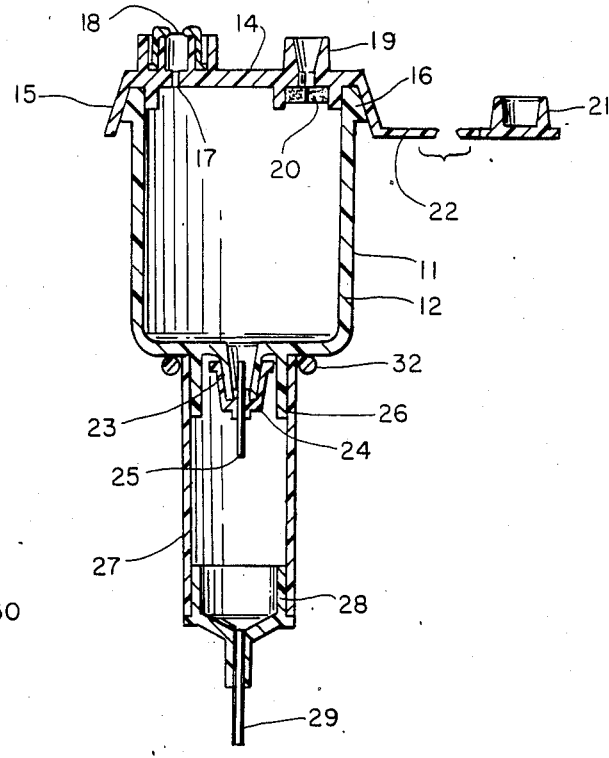
FIG. 2 is an enlarged central vertical section taken on line 2—2 of FIG. 3.
Figure 3:
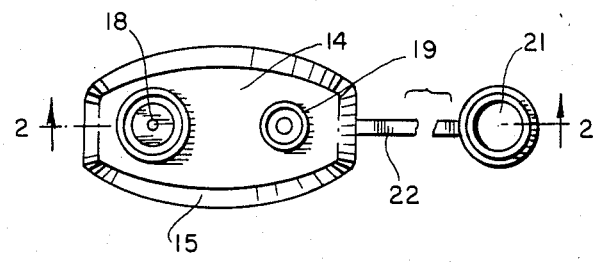
FIG. 3 is a plan view of the device as illustrated in FIG. 2.
Figure 8:
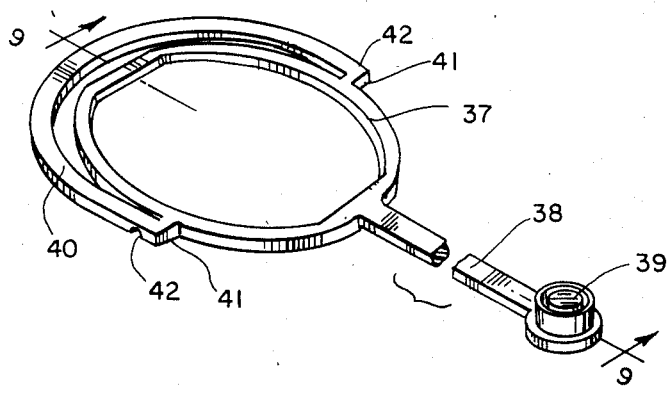
FIG. 8 is a perspective view showing another modification of the hanging means.
Figure 9:
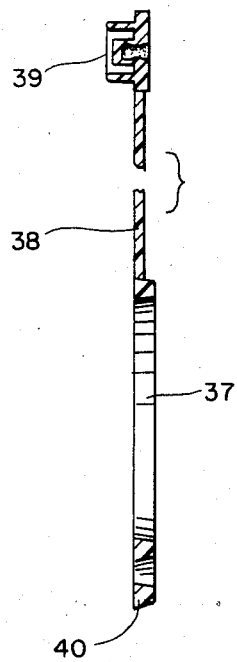
FIG. 9 is a vertical section taken on line 9—9 of FIG. 8.

FIGS. 2A, 8 and 9 of the drawings show a modification of the hanger means in which a substantially oval loop 37 is formed integrally with a flexible tether 38 carrying a closure cap 39 for the filling port 19 at its free end. An arcuate hanger element 40 is also united with the oval loop 37 by a pair of opposite side lugs 41 and the hanger element has notches 42 formed therein close to the lugs 41. The notches 42 locally reduce the thickness of the element 40 near the lugs 41 and form hinge joints for the hanger element 40.

The oval loop 37, FIG. 2A, slips onto the molded minicontainer 11 and engages beneath the skirt 15 of container top 14. The arcuate hanger element 40 can then be swung up on its hinge axis to a vertical use position similar to that shown in FIG. 1 for the hanger loop 33. An advantage of the hanger construction shown in FIGS. 2A, 8 and 9 is that the closure cap 39 and tether 38 are formed integrally with the oval loop 37 instead of with the container top. Also, the hinged hanger element 40 is considerably shorter than the hanger loop 33 whose ring 32 is at the bottom of the container 11 instead of near its top.

It is to be understood that the forms of the invention herewith shown and described are to be taken as preferred examples of the same, and that various changes in the shape, size and arrangement of parts may be resorted to, without departing from the spirit of the invention or scope of the subjoined claims.

I claim:

1. A self-contained solution set comprising a solution container having a filtered air vent and a valved filling port to enable filling the container by means of a syringe without needle, a drip device on the bottom of the container, a drip chamber means on the bottom of the container enclosing the drip device, an infusion tube assembly connected to the bottom of said drip chamber means, a hanger means for the solution set, said hanger means supporting said solution container by an adjacent support member, said support member having a hanger hinged thereto, the support member of the hanger means comprising a support ring at the bottom of the solution container surrounding and encircling the drip chamber means, and said hanger comprising a hanger loop hingedly attached to the support ring by integral flexible hinges and having side portions adapted to straddle side walls of the solution container.

2. A self-contained solution set as defined in claim 1, and the filtered air vent and valved filling port being located on the top of the solution container.

3. A self-contained solution set as defined in claim 1, and the drop chamber means comprising a tubular drip chamber having one end coupled with a sleeve on the bottom of the solution container and its other end coupled with the infusion tube assembly through an adapter thereof.

4. A self-contained solution set as defined in claim 1, and said air vent and valved filling port being located on one side of the solution container near its top.

5. A self-contained solution set as defined in claim 1, and the solution container comprising a small container having a solution capacity of approximately 50 ml.

6. A self-contained solution set as defined in claim 1, and the solution container comprising a molded container including a body portion and a container top for the body portion and being hermetically sealed thereto, and said filtered air vent and valved filling port being located on said container top.

7. A self-contained solution set as defined in claim 6, and a tethered closure cap for the valved filling port on the container top.

8. A self-contained solution set as defined in claim 1, wherein said flexible hinges are attached to said support ring by side ears on said support ring.

9. A self-contained mini-solution set particularly for administering secondary medications comprising a small graduated solution container having a solution capacity of about 50 ml., a filtered air vent and a valved filling port on the solution container near its top, the bottom of the solution container having a solution outlet nipple, a drip device coupled with said nipple, a drip chamber element surrounding the drip device and being coupled to the bottom of the solution container, an infusion tube assembly coupled to the drip chamber element, a hanger means for the mini-solution set for supporting the solution container, said hanger means supporting said solution container by an adjacent support member, said support member having a hanger hinged thereto, said support member of the hanger means comprising a support loop surrounding said solution container, said solution container having an abutment surface near its top and said support loop engaging beneath the abutment surface, a tethered closure cap for said valved filling port on said support loop, and said hinged hanger attached on the support loop by integral flexible living hinge means and adapted to be elevated to a use position above the top of said solution container.

10. A self-contained solution set as defined in claim 9, wherein said flexible living hinge means comprises a pair of opposite side lugs on said support loop, and the hinged hanger has notches formed therein close to said lugs.

11. A self-contained mini-solution set comprising a container including a body portion, a container top hermetically sealed to the body portion and having a skirt projecting outwardly from the side wall of the body portion, a filtered air vent and a valved filling port on the container top, a drip device on the bottom of the container body portion, a drip chamber means on the bottom of the container body portion enclosing the drip device, an infusion tube assembly connected to the bottom of said drip chamber means, a hanger means for the mini-solution set comprising a support loop surrounding the container body portion and engaging supportively beneath said skirt, a tethered closure cap for the valved filling port on the support loop, an arcuate hanger element on said support loop and being hingedly secured thereto by integral hinge means, said support loop, tethered closure cap and arcuate hanger element being integrally formed of compliant material, and said integral hinge means including said hanger element having notches therein adjacent said support loop.

* * * * *